United States Patent
Acharya et al.

(12) 
(10) Patent No.: US 6,210,699 B1
(45) Date of Patent: Apr. 3, 2001

(54) ORAL TRANSMUCOSAL DELIVERY OF DRUGS OR ANY OTHER INGREDIENTS VIA THE INNER BUCCAL CAVITY

(75) Inventors: Ramesh N. Acharya; Joseph L. Baker, both of Salt Lake City, UT (US)

(73) Assignee: Watson Pharmaceuticals, Inc., Corona, CA (US)

( * ) Notice: Subject to any disclaimer, the term of this patent is extended or adjusted under 35 U.S.C. 154(b) by 0 days.

(21) Appl. No.: 09/285,018

(22) Filed: Apr. 1, 1999

(51) Int. Cl.⁷ .............................. A61F 13/02; A61K 47/30
(52) U.S. Cl. ......................................... 424/435; 514/772.3
(58) Field of Search ........................... 424/435; 514/772.3

(56) References Cited

U.S. PATENT DOCUMENTS

| | | |
|---|---|---|
| 4,112,066 | 9/1978 | Jiles . |
| 4,292,028 | 9/1981 | Barr . |
| 4,303,648 | 12/1981 | Witzel . |
| 4,409,202 | 10/1983 | Witzel . |
| 4,597,959 | 7/1986 | Barr . |
| 4,740,365 | 4/1988 | Yukimatsu . |
| 4,997,852 | 3/1991 | Minton . |
| 5,008,291 | 4/1991 | Minton . |
| 5,010,107 | 4/1991 | Minton . |
| 5,431,918 | 7/1995 | Ferrero . |
| 5,700,478 | 12/1997 | Biegajski et al. . |

Primary Examiner—Carlos A. Azpuru
(74) Attorney, Agent, or Firm—Thorpe North & Western LLP

(57) ABSTRACT

A device and method for the oral transmucosal delivery of active substances to the oral cavity utilizing an unplasticized polyvinyl pyrrolidone polymer (PVP) as the primary mucoadhesive. The device is applied and adheres to the mucosa of the oral cavity without causing side effects or leaving an unpleasant taste. Preferably the device is a bilayer tablet having a mucoadhesive layer and an overlying active substance containing layer. The mucoadhesive layer may contain PVP as the only adhesive or may be combined with other hydrophilic polymeric substances. The active layer also contains a hydrophilic polymer carrier. The layers in the device dissolve and release the active substance to the oral cavity and is particularly adapted for the delivery of substances active in the oral cavity such as breath fresheners and substances to combat dry mouth. It is also useful for the delivery of ionic drugs such as peptides.

47 Claims, No Drawings

ORAL TRANSMUCOSAL DELIVERY OF DRUGS OR ANY OTHER INGREDIENTS VIA THE INNER BUCCAL CAVITY

BACKGROUND OF THE INVENTION

This invention relates to a composition and a method for oral transmucosal delivery of active substances to a human or animal via the inner buccal cavity. More particularly, this invention relates to an improved dosage form which can easily adhere to the inner buccal cavity and sustain transmucosal release of drugs, odorants or any other ingredients and exhibit the activity effectively.

The sustained delivery of certain active substances, especially ionic peptide-based drugs, presents one of the greatest challenges in pharmaceutical science. Oral administration of pharmaceutical compositions has some drawbacks. For instance, it is difficult to keep the medicament at the desired location so that it can be absorbed, it is easily metabolized in the liver, and it is easily decomposed in the stomach. Accordingly, there has been much interest in the use of the mucosal lining of body cavities, for example the oral cavity, as the site of administration of active substances. Both the buccal and sublingual membranes offer advantages over other routes for administration. For example, drugs administered through the buccal and sublingual routes have a rapid onset of action, reach high levels in the blood, avoid the first-pass effect of hepatic metabolism, and avoid exposure of the drug to fluids of the gastrointestinal tract. Additional advantages include easy access to the membrane sites so that an active substance containing device can be applied, localized, and removed easily. Further, there is good potential for prolonged delivery through the mucosal membrane. M. Rathbone & J. Hadgraft, 74 *Int'l J. of Pharmaceutics* 9 (1991).

The sublingual mucosa includes the membrane of the ventral surface of the tongue and the floor of the mouth, whereas the buccal mucosa constitutes the lining of the cheek. The sublingual mucosa is relatively more permeable than the buccal mucosa, thus giving rapid absorption and acceptable bioavailability of many active substances. Furthermore, the sublingual mucosa is convenient, accessible, and generally well accepted. This route has been investigated clinically for the delivery of a substantial number of drugs. It is the preferred route for administration of nitroglycerin and is also used for buprenorphine and nifedipine. D. Harris & J. Robinson, 81 *J. Pharmaceutical Sci.* 1 (1992).

The buccal mucosa is less permeable than the sublingual mucosa. The rapid absorption and high bioavailabilities seen with sublingual administration of drugs is not generally provided to the same extent by the buccal mucosa. D. Harris & J. Robinson, 81 *J. Pharmaceutical Sci.* (1992) at 2. The permeability of the oral mucosa is probably related to the physical characteristics of the tissues. The sublingual mucosa is thinner than the buccal mucosa, thus permeability is greater for the sublingual tissue. The palatal mucosa is intermediate in thickness, but is keratinized thus lessening its permeability, whereas the other two tissues are not.

The ability of molecules to permeate through the oral mucosa appears to be related to molecular size, lipid solubility, ionization and many other factors. Small molecules, less than about 100 daltons, appear to cross the mucosa rapidly. As molecular size increases permeability decreases rapidly. Lipid-soluble compounds are more permeable through the mucosa than are non-lipid-soluble molecules. In this regard, the relative permeabilities of molecules seems to be related to their partition coefficients. The degree of ionization of molecules, which is dependent on the $pK_a$ of the molecule and the pH at the membrane surface, also greatly affects permeability of the molecules. Maximum absorption occurs when molecules are unionized or neutral in electrical charge and absorption decreases as the degree of ionization increases. Therefore, charged drugs, such as ionized polypeptide based drugs, present a significant challenge to absorption through the oral mucosa.

For a number of practical purposes it can be useful to affix a device containing an active substance within a mucosal-lined body cavity, such as the oral cavity. For example, conventional forms of substance delivery such as a lozenge, troche, breath freshener, mouth wash or spray work by shedding or admixing the substance into the saliva, which bathes the tissues of the oral cavity and throat as it passes posteriorly towards the esophagus. Such forms remain in the oral cavity only for short periods of time, generally not more than about 10 to 20 minutes, and they cannot always provide for effective sustained delivery of the substance. Moreover, the presence of a lozenge or troche in the user's mouth can be annoying or distracting, and may interfere with speech or with the ingestion of fluids. Holding the lozenge in the mouth to avoid either swallowing it or spitting it out requires conscious effort, and inadvertent loss can be embarrassing.

There are numerous instances where the active substance is intended for use at the site of delivery rather than absorption through mucosal membranes for systemic use. For example breath fresheners for the treatment of, or as a prophylactic against, halitosis, or agents for the treatment of xerostomia (dryness of the mouth) function directly in the oral cavity rather than through absorption. However, it would be desirable to have such agents held in place in the oral cavity to avoid the problems associated with lozenges or troches as noted above.

Various bioadhesives have been proposed for use in establishing adhesive contact with mucosal surfaces. See, for example, Biegajski, U.S. Pat. No. 5,700,478; Lowey, U.S. Pat. No. 4,259,314; Lowey, U.S. Pat. No. 4,680,323; Yukimatsu et al., U.S. Pat. No. 4,740,365; Kwiatek et al., U.S. Pat. No. 4,573,996; Suzuki el al., U.S. Pat. No. 4,292,299; Suzuki et al., U.S. Pat. No. 4,715,369; Mizobuchi et al., U.S. Pat. No. 4,876,092; Fankhauser et al, U.S. Pat. No. 4,855,142; Nagai et al., U.S. Pat. No. 4,250,163; Nagai et al., U.S. Pat. No. 4,226,848; Browning, U.S. Pat. No. 4,948,580; Schiraldi et al., U.S. Reissue Patent Re.33,093; and J. Robinson, 18 *Proc. Intern. Symp. Control. Rel. Bioact. Mater.* 75 (1991). Typically, these adhesives consist of a matrix of a hydrophilic, e.g., water soluble or swellable, polymer or mixture of polymers which can adhere to wet mucosal surfaces. Such polymers are inclusive of hydroxypropyl cellulose, hydroxypropyl methylcellulose, hydroxy ethylcellulose, ethylcellulose, carboxymethyl cellulose, dextran, gaur-gum, polyvinyl pyrrolidone, pectins, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, and the like. These adhesives may be formulated as ointments, thin films, tablets, troches, and other forms. Often, these adhesives have had medicaments mixed therewith to effectuate slow release or local delivery of a drug.

However, these known bioadhesives have several drawbacks. For example, adhesives in the form of pastes, creams or ointments are messy and inconvenient to use, and generally adhere poorly or not at all and are not suitable for extended periods of use. Some forms of adhesives, such as Carbopol (carboxyvinyl polymers), are not water soluble thus leave a tacky, greasy residue in the oral cavity of the wearer, and can cause sustained oral irritation. In addition, Carbopol based adhesives are ionic polymers which interact with ionic active substances, such as ionic polypeptide based drugs, and can inhibit absorption of such active substances. On the other hand, some forms of adhesives remain in the oral cavity for only short periods of time, e.g. generally not more than about 10 or 20 minutes, and therefore cannot provide for delivery of a substance over an extended period of time.

Improved adhesives have been attained by using sodium alginate to overcome some of the problems associated with Carbopol based adhesives. However, sodium alginate is also an anionic polymer that shows ionic interaction with cationic active substances. Therefore, to formulate an adhesive having little or no interaction with ionic active substances, such as ionic polypeptide based drugs, would be highly desirable.

It has been discovered that polyvinyl pyrrolidone (PVP), without the presence of a plasticizer, used alone or in combination with other polymers or copolymers, has sufficient adhesion properties to the oral mucosa and also to polyacrylic denture materials to function surprisingly well to adhere devices containing active substances to the oral cavity. Since PVP is a non-ionic compound, a PVP-based mocoadhesive does not interact with ionic active substances. Moreover, PVP-based adhesives show a significant reduction in irritation of mucosa in human trials, compared to Carbopol-based adhesives. Although plasticized PVP has been used as an ingredient of bioadhesive compositions in prior art, a non-plasticized PVP based mucoadhesive has not heretofore been taught or suggested. In addition, the non-plasticized PVP based mucoadhesives of this invention show an improved stability when compared with prior mucoadhesives.

U.S. Pat. No. 4,740,365 discloses a sustained-release mucoadhesive preparation that may consist of one or two layers. However, the mucoadhesive layer is always a combination of two polymers components with a ratio of 95:5 to 5:95. One polymer component comprises one or more polymers selected from polyvinylpyrrolidone, polyvinyl alcohol, polyethylene glycol, alginic acid or a salt thereof, and an alternating copolymer of maleic anhydride and methyl vinyl ether. The other polymer component comprises one or more polymers selected from polyacrylic acid or a salt thereof. One aspect of the invention is to combine the two polymer components to maximize adhesive properties. U.S. Pat. No. 5,700,478 discloses a water-soluble pressure-sensitive adhesive including a water-soluble polymer that is made tacky at room temperature by addition of a water-soluble plasticizer that is miscible with the polymer. The presence of the plasticizer negatively affects the palatability and stability of the mucoadhesive. In addition to undesirable interaction with the ionic active substances, the presence of plasticizers or other ionic polymers in the mucoadhesive may also cause undesirable wearing properties or irritation.

Therefore, there is a need for a mucoadhesive that does not interact with ionic active substances and does not affect the palatability of the adhesive. The non-plasticized PVP-based mucoadhesive of the present invention also simplifies and reduces the cost of manufacture. In addition, a non-plasticized PVP-based mucoadhesive of this invention also reduces the unpleasant flavor and oral irritation associated with plasticizers or other copolymers.

OBJECTS AND SUMMARY OF THE INVENTION

It is an object of the present invention to provide a transmucosal delivery device which can adhere to the inner buccal cavity or palate for the delivery of active substances.

It is another object of the present invention to provide a transmucosal device for the delivery of active substances utilizing a mucoadhesive that is fully soluble in the secretions present in buccal cavity without having an objectionable taste or causing irritation.

It is also an object of the invention to provide a transmucosal device for the delivery of active substance utilizing a nonionic mucoadhesive thereby providing methods for administering both charged and uncharged active substances to humans and animals that allows easy accessibility to the site of administration.

It is a further object of the invention to provide dosage forms and methods for administering charged and uncharged active substances to humans and animals that allows for localization of the dosage form in the oral cavity over a sustained period to maximize active substance effects utilizing a mucoadhesive that dissolves in secretions present in the body cavities without having an objectionable taste or causing irritation.

It is still another object of the present invention to provide a transmucosal device for the delivery of active substances in a dosage form utilizing a nonionic mucoadhesive that provides for a method for administering charged and uncharged active substances to humans and animals wherein the device has acceptable tissue compatibility.

It is yet another object of the invention to provide a transmucosal device for the delivery of active substances utilizing a nonionic and nonplasticized mucoadhesive thereby providing a method for administering charged and uncharged active substances to humans and animals through the buccal and sublingual mucosa that avoids the objectionable taste or irritation associated with plasticized or ionic mucoadhesives.

These and other objects may be accomplished by a laminated active substances delivery device comprising a layer of mucoadhesive composition consisting primarily of PVP without a plasticizer. The non-plasticized PVP mucoadhesives of this invention can adhere to the inner buccal cavity or palate for delivering both charged and non-charged active substances. Such non-plasticized PVP mucoadhesives provide for localization of the active substance-containing delivery device over a sustained period to maximize drug effect and then dissolve in the secretions present in the buccal cavities without having an objectionable taste or causing irritation. The non-plasticized PVP mucoadhesive has sufficient adhesion not only to mucosal membranes but also to a variety of materials, such as polyacrylic denture material.

This invention therefore provides dosage forms having an adhesive surface suitable for affixing to the mucosal surface of the inner buccal cavity. In some dosage forms, the non-plasticized PVP mucoadhesive serves as a reservoir for the substances to be delivered, and releases the substances into the oral cavity as the adhesive dissolves. The active substance absorption also occurs via diffusion of the active substance through the adhesive layer of the device into the mucosal membrane. In some configurations a laminated device includes at least one active polymer layer in addition to the base mucoadhesive layer. Each layer may release one or more substances according to a desired timed delivery regime, for example, delayed onset delivery, pulsed delivery, and sequential delivery. The invention is particularly useful to deliver ionic active substance because the non-plasticized PVP mucoadhesives do not interact with ionic active substances and to the delivery of active substances intended for use directly in the oral cavity such as breath fresheners and saliva enhancing agents. The invention is uniquely suited to the delivery of breath freshening agents to the oral cavity particularly when the mucoadhesive layer is adhered to the hard palate or roof of the mouth.

DETAILED DESCRIPTION OF THE INVENTION

For the purposes of this disclosure the following definitions will apply:

"Active substance," "drugs" or "agents" refers to all functional compounds which are desirable to be delivered via oral cavity, either charged or non-charged, including but not limited to, medicaments for oral diseases, diseases of the teeth and also systemic diseases, oral odorants such as breath freshening agents, saliva stimulants, nutritional supplements such as vitamins, herb extracts or minerals, and mixtures thereof. For example, odorants suitable for masking or refreshing objectionable breath including peppermint, spearmint, menthol, grape, cherry, lemon, strawberry, orange, licorice, lime and any mixtures thereof. Active substances to be delivered by the device of the present invention includes ionic or non-ionic drugs for oral or systemic diseases, for example, peptide drugs (e.g. calcitonin, DDAVP), analgesics and anti-inflammatory agents (e.g. indomethacin, ibuproden), mouth disinfectants (chlorohexidine hydrochloride, hexylresorcine), cardiovascular agents (e.g. nitroglycerin, isosorbide dinitrate, nifedipine), antiasthmatics (e.g. disodium cromoglycate), antibiotics (e.g. penicillin, erythromycin), chemotherapeutics (e.g. sulfathiazole, nitrofurazone), local anesthetics (e.g. benzocaine), cardiotonics (e.g. digitalis, digoxin), antitussives and expectorants (e.g.codeine phosphate, isoproterenol hydrochloride), agents affecting digestive organs, antihistamines, anti-inflammatory steroids, hemostatics, sexual hormones, sedatives, antitumor agents, or the like.

"Mucoadhesive," refers to hydrophilic polymers, natural or synthetic, which, by the hydrophilic designation, can be either water soluble or swellable and which are adhesive to mucosal surfaces. Preferably such adhesives adhere the active substances-containing formulation to the mucosal tissues as well as functioning as a reservoir of active substances which can be dissolved or absorbed via contacting the mucosal membrane.

"PVP", "polyvinylpyrrolidone", "PVP mucoadhesive", "non-plasticized PVP mucoadhesive" and the like refers to a mucoadhesive composition consisting essentially of PVP polymer that does not contain any plasticizers. Polyvinylpyrrolidone is a homopolymer of 1-ethenyl-2pyrrolidinone and is available in various grades under the generic or tradename "Povidone". Mixtures of one or more grades or molecular weights of PVP polymers may be utilized. Preferably PVP polymers will have an average molecular weight of between about 10,000 and 700,000. Other functionally suitable hydrophilic ionic or nonionic polymers or copolymers conventionally used in adhesive formulations may be combined with the nonplasticized PVP depending on use. If the substance to be delivered is nonionic it may not be disadvantageous to utilize some ionic polymers or copolymers. On the other hand, when delivering an ionic substance, it is preferred that an added hydrophilic polymer be nonionic. Typical of hydrophilic polymers or copolymers that may be combined with PVP include acrylic acid polymers, e.g. carboxyvinyl or carboxymethylene polymers such as sold under the generic of tradenames "Carbomer" and "Carbopol"; hydroxypropyl cellulose such as sold under the tradename "Klucel"; methylcellulose such as sold under the tradename "Methocel" and polyethylene oxide polymers such as sold under the tradename "Polyox".

"Permeation enhancer," "enhancer," "penetration enhancer," or similar term means a material that achieves such permeation enhancement, and an "effective amount" of an enhancer means an amount effective to enhance penetration through the mucosa of a selected agent to a selected degree. Taurocholic acid and its salts are exemplary of transmucosal enhancers.

This invention features a laminated active substance delivery system which includes at least one active substance containing polymer layer in addition to a mucoadhesive polymer layer which may also contain active substances. The system releases one or more substances according to a desired time delivery regime. For example, onset of release may be delayed following placement of the delivery system within the body cavity, or a substance may be released at different rates over time, or in pulses with intervening periods in which essentially no release occurs. Alternatively, two or more substances may be sequentially released, with or without an intervening period in which no substance is released. The pattern of release is established by the sequential arrangement of laminates containing the substances, and the concentration of the substances contained in the various layers.

The mucoadhesive composition of this invention consists primarily of nonplasticized PVP. The mucoadhesive can be 100% PVP. However, when an additional polymer or copolymer is used in the mucoadhesive composition, the ratio of PVP to such other polymers or copolymers will be at least 1:1 and will be preferably between 1:1 and 20:1. In other words, nonplasticized PVP will make up between about 50 to 95% by weight of the mucoadhesive composition with the remaining 5 to 50% by weight being a functionally suitable polymer or copolymer.

The mucoadhesive composition will make up between about 20–99% by weight of the adhesive layer the with remaining 1 to 80% by weight being a member selected from the group consisting of water soluble compounding agents and any active substances added to the adhesive layer. By "compounding agents" is meant inert ingredients or formulation aids such as lactose, mannitol, magnesium stearate, flavoring agents, coloring agents, stabilizers, binding agents, or any other fillers which do not have a negative impact on the function of the mucoadhesive layer. The non-plasticized PVP mucoadhesives are fully water-soluble, and are thus fully soluble in secretions present in oral mucosa without having an objectionable taste or causing sustained irritation. In addition, the non-plasticized PVP mucoadhesives are nonionized and thus are particularly useful to affix a transmucosal delivery formulation for ionic active substances such as polypeptide drugs.

The mucoadhesives of this invention can be used to affix any oral delivery device within the oral cavity, e.g. patches, tablets, and the like. It is particularly useful in construction of a laminated or multi-layered device for controlled delivery of substances within the oral cavity. The non-plasticized PVP mucoadhesive layer can serve as a reservoir for the active substances to be delivered, and releases the substance into the oral cavity as the adhesive dissolves. The substances can also be transmucosally absorbed through the adhesive layer which is in contact with an oral mucosal membrane.

While laminated or multilayered devices will be described with more particularity below, the release rate of an active substance from a particular layer is determined basically by the rate at which the layer dissolves or disperses in the fluid milieu of the oral cavity, and by the diffusion rate of the active substance from particular layer which is dependent upon the concentration of the active substances within the layer. Release from a more basally situated layer may be delayed by an overlaying layer(s), and the duration of the delay in delivery from such a particular layer is determined basically by the time required for the overlaying layer(s) to disperse. The active substances contained in the adhesive layer can also be absorbed via the contacting mucosal membrane and the absorption may be enhanced by addition of a suitable penetration enhancer into the formulation of either the adhesive layer or an active or overlying layer or both. The concentration of the active substance will be an "effective amount," which is the amount required to achieve the desired delivery either into the oral cavity and/or across mucosal tissues at a rate and for a time which will achieve the desired physiological effect. Those concentrations can be readily determined by the practitioner based upon the active substance selected.

As an indication of the variances in active substance concentration in the mucoadhesive layer which may provide "effective amounts," it is readily apparent that the active substance concentration will, of necessity, be determined by the active substance being utilized and its potency and/or bioavailability. For example, when the active substance is a drug an effective amount will be much smaller than when the active substance is a breath freshener. Effective amounts of an active drug substance may be as little as 0.1% and may be as much as 10% of the mucoadhesive layer. Preferably amounts will be between about 0.2 and 5.0% by weight. On the other hand, effective amounts of breath fresheners vary from about 10 to 60% by weight of the mucoadhesive layer with amounts of between about 20 and 50% being preferred.

As previously stated, the pressure-sensitive mucoadhesive composition of the mucoadhesive layer consists essentially of nonplasticized PVP or a combination of PVP and suitable polymers or copolymers. The concentration of mucoadhesive in the layer will be between about 20 and 99% by weight. Preferably the mucoadhesive concentration is between about 30 and 80%. The remaining amounts are made up from one or more members selected from the group consisting of water soluble compounding agents and any active substances. Such compositions show sufficient adhesion to oral mucosal surfaces of animals such dogs and also to humans and to denture materials. The non-plasticized PVP mucoadhesives of this invention are water soluble, and are capable of conforming to and adhering to contoured surfaces such as the gums, the roof of the mouth and buccal lining of the mouth. Such mucoadhesives can be used as part of a system for delivery of substances through the oral mucosa (as a buccal transmucosal patch), for delivery of substances into the oral cavity itself, or the combination of both via a laminated configuration, which may be either in the form of a tablet or patch. Both patches and tablets are prepared such that the mucoadhesive layer contains the non-plasticized PVP adhesive which may or may not contain a drug/enhancer, while the other layer(s) is non-adhesive, at least on the outer surface, and contains one or more drugs/enhancer combinations, breath fresheners or other active substances.

One preferred embodiment of this invention features a layered composite for delivery of an active substance into the oral cavity, having an outer active layer that includes the active substances dispersed or dissolved in a water soluble polymer, and the above-described water soluble mucoadhesive layer. Also as noted above, the rate of release of the active substance within the oral cavity depends partially on the rate of dissolution or dispersion of the polymer of the active layer. As previously mentioned, active substances may also be included in the adhesive layer which may be released with the dissolution of the adhesive layer, and be absorbed by the contacting mucosal membrane as well.

The active or outer layer of a bilayer or multilayer system is laminated to the mucoadhesive layer by conventional techniques. The active layer is also based on the presence of a water soluble polymer in which is dispersed the active substance to be delivered along with other compounding agents such as referenced above. Preferably the water soluble polymer will be present in amounts of between about 3 and 60% by weight of such hydrophilic polymers or copolymers. Typical of hydrophilic polymers or copolymers that may be used in the active layer include those mentioned above for use in the mucoadhesive layer such as acrylic acid polymers, hydroxypropyl cellulose, methylcellulose, polyethylene oxide and polyvinyl pyrrolidone, as well as natural polymers such as gaur-gum, pectins, starches, gelatin, casein and the like. These water soluble polymers are compatible with the active substances to be delivered. Preferably such polymers are selected to promote desired active substance release profiles and do not adversely affect the activity of such substance.

The active or overlying layer(s) will contain an "effective amount" of the active substance being delivered. As in the mucoadhesive layer, the effective amount of active substance will be determined by the active substance being utilized and its potency and/or bioavailability. Those amounts may be the same as in the mucoadhesive layer but may be higher when the mucoadhesive layer is utilized primarily to secure a device to the oral mucosa. For example, when the active substance is a drug an effective amount will be much smaller than when the active substance is a breath freshener. Effective amounts of an active drug substance may be as little as 0.1% and may be as much as 10% of the mucoadhesive layer. Preferably amounts will be between about 0.2 and 5.0% by weight. On the other hand, effective amounts of breath fresheners vary from about 1 to 60% by weight of the mucoadhesive layer with amounts of between about 5 and 40% being preferred.

The active layer may also contain from between about 40 and 99.9% by weight of compounding agents as defined above.

The active substance delivery system of this invention is particularly useful for administering a substance over an extended time period for relief of oral symptoms such as bad breath, sore throat, cough, dry mouth or other similar symptoms.

For example, odorants suitable for masking or refreshing objectionable breath include agents such as mint, spearmint, menthol, grape, cherry, lemon, strawberry, orange, licorice, peppermint, lime and any mixtures thereof. Other substances which are suitable for being transmucosally administered by the delivery system of this invention include but are not limited to saliva stimulants, nutritional supplements such as vitamins, herb extracts or minerals, and mixtures thereof.

The device of the present invention is also suitable for transmucosally delivery of both ionic or non-ionic drugs for oral or systemic diseases including analgesics and anti-inflammatory agents (e.g. indomethacin, ibuproden), mouth disinfectants (chlorohexidine hydrochloride, hexylresorcine), enzymes (e.g. nitroglycerin, isosorbide dinitrate, nifedipine), antiasthmatics (e.g. disodium cromoglycate), antibiotics (e.g. penicillin, erythromycin), chemotherapeutics (e.g. sulfathiazole, nitrofurazone), local anesthetics (e.g. benzocaine), cardiotonics (e.g. digitalis, digoxin), antitussives and expectorants (e.g.codeine phosphate, isoproterenol hydrochloride), agents affecting digestive organs, antihistamines, antiinflammatory steroids, hemostatics, sex hormones, sedatives, antitumor agents, or the like. Effective amounts, i.e. from 2 to 20% by weight, of penetration enhancers such as a salt of a conjugate of a bile acid with taurine or taurocholic acid may be optionally added in the active layer to enhance the penetration of the active drug.

The most preferred embodiment of this invention features a laminated device for administering an active agent into the oral cavity over an extended period of time and having the device dissolve without leaving an objectionable taste or cause-sustained irritation to the oral cavity. The device can be either a laminated film or tablet, having at least two layers, including a basal layer of a pressure-sensitive, water-soluble, non-plasticized PVP mucoadhesive composition, which may or may not contain an active agent, and an active agent containing water soluble polymer layer. The device is affixed to the mucosal surface, preferably the palatine surface of the oral cavity via the mucoadhesive layer of the device.

As previously stated, the systems utilized in the present invention comprise an active layer containing the active substances and a basal mucoadhesive layer which may also contain an active substance. The systems may be in either the form of a tablet or a patch. Bilayer tablets are made by classical bilayer tablet compression techniques on a suitable press. Layers of a bilayer tablets consisting of an active non-adhesive layer and an adhesive layer may contain layers which are of different colors to distinguish the layers for purposes of application. The identification of the active non-adhesive layer facilitates application by the patient and prevents incidental adhesion of other oral tissues to the tablet. The active layer is prepared by dry mixing the ingredients and compressing them into a tablet or by wet granulating the ingredient mixture and then compressing according to accepted pharmaceutical techniques. In general, it has been found suitable to mix the active substances, polymer and any formulation aids such as magnesium stearate, lactose, flavors, and the like and then compress the mix in a press at about 0.2–0.5 tons for a dwell time of 0.2–10 seconds.

The adhesive layer is first prepared by intimately admixing PVP, copolymers, and tableting excipients and binding compounds such as sorbitol, dyes, flavors, magnesium stearate, mannitol and the like. This may be formulated as a dry mix or accomplished by conventional wet granulation and screening techniques followed by drying. In either event, the blended adhesive layer ingredients are then placed on top of the partially compressed active layer and both layers are then compressed at a higher pressure, for example from 0.5 to 1.5 tons for an additional 2–10 seconds dwell time.

In some embodiments the active substance is an odorant such as an essential oil of a plant material, a refined fraction of an essential oil, or a combination of the chief aromatic constituents of an essential oil. Preferably, the odorant is a mint such as obtained from oils of peppermint, spearmint or wintergreen. Any other suitable odorant or masking agent may also be used such as menthol, grape, cherry, lemon, strawberry, orange, licorice, lime and any mixtures thereof. In other embodiments the active substances may be saliva stimulants, or nutritional supplements such as vitamins, herb extracts or minerals, and mixtures thereof.

The systems of the present invention will preferably be sized to provide a device having a contact surface area of between about 0.5 to 10 $cm^2$ for adhering the adhesive layer and the mucosal surface. Areas of between about 0.5 to 5 $cm^2$ are preferred with areas of between about 1.0 and 5 $cm^2$ being optimal. The active mucoadhesive layers will generally have a thickness of between about 0.1 and 3 mm with thicknesses of between about 0.5 and 2 mm being preferred.

Extended delivery of active substances can be obtained according to the bilayered or multilayered device according to the present invention. The rate of release of the active substances within the oral cavity can be specified by selection of particular polymer or polymer combinations. The device according to the present invention is capable of adhering to contoured surfaces such as the gum or the roof of the mouth. The device can deliver the active substances over a period of up to 2 hours or longer from a single device, and can dissolve without leaving any bad taste or causing sustained irritation. The device according to this invention is particularly useful in delivering charged drugs such as polypeptide based drugs because the PVP mucoadhesive is non-ionic which does not interact with ionic drugs to be delivered. Further, the device is particularly adaptable for the delivery of odorants or other active agents for the treatment of halitosis or dryness of the mouth.

The following examples are illustrative of methods of preparing both bilayer tablets.

EXAMPLE 1

With the proviso that the mucoadhesive layer must contain the above designated percent by weight of a PVP or a PVP and copolymer combination, bilayered breath freshener tablets are prepared in the following manner containing the designated ingredients within the ranges specified. An active layer is prepared by transferring the specified amounts of the following ingredients into a V blender

| Ingredients | Weight Percentage Range (%) |
| --- | --- |
| Mint Powder | 1–80 |
| co-polymer | 5–70 |
| Sweetener | 0.1–20 |
| Magnesium Stearate | 0.1–10 |
| Mannitol | 0–80 |
| Dye | 0.1–0.8 | and blended for a specified amount of time. In certain instances, where liquid flavorings are utilized, it is necessary to mix the blended material in a suitable low shear mixer along with the flavoring agent. The blended material is then discharged into a suitable container. The active layer blend is then passed through the Fitzmill using the specified screen. Dye and magnesium stearate are added and blended for a specified amount of time.

An adhesive layer is prepared by transferring the specified amounts of the following ingredients into a V blender:

| Ingredients | Weight Percentage Range (%) |
| --- | --- |
| Mint Powder | 1–80 |
| PVP | 20–90 |

-continued

| Ingredients | Weight Percentage Range (%) |
|---|---|
| Carbopol | 0–4.8 |
| co-polymer | 0–80 |
| Sweetener | 0.1–20 |
| Mannitol | 0–80 | and blended for a specified amount of time. The blended materials are then discharged into a suitable container. The adhesive layer blend is then passed through the Fitzmill using the specified screen. The specific amount of magnesium stearate is calculated based on the yield of the adhesive layer blend (0.5–10% by weight), and then added to the blender and blended for a specified amount of time. The final blended materials are collected into tared polyethylene lined containers.

The tablet press was set up for bi-layered operation using the specified parameters. The final blended powder for the active layer granulation was placed in the first hopper and the adhesive granulation was placed into the second hopper. The tablet press was set to a specified amount of active layer prior to introducing the specified amount of the adhesive granulation. The compressed tablets were packaged into bottles and labeled with the proper information.

The following are exemplary of other oral transmucosal (OTM) tablet formulations which are within the scope of this invention. However, they are illustrative only and are not intended to define the scope of the invention. These tablets can be conveniently formulated according to the method described in Example 1.

EXAMPLE 2

This example illustrates a bilayer oral transmucosal tablet for rapid onset delivery of drugs formulated according to the method described in Example 1. The drug to be delivered in this example is Buprenorphine HCL and the penetration enhancer is taurocholic acid. The adhesive layer contains 60% non-plasticized PVP.

Buprenorphine HCL Rapid Onset

| Active Layer | % w/w | Adhesive Layer | % w/w |
|---|---|---|---|
| Buprenorphine HCL | 0.86 | Mannitol | 39.25 |
| Mannitol | 70.66 | Povidone K90 | 40.00 |
| Taurocholic Acid | 4.00 | Povidone K30 | 20.00 |
| Klucel HXF | 10.00 | Magnesium Stearate | 0.75 |
| Povidone K30 | 5.00 | | |
| Sod. Bicarbonate | 8.57 | | |
| Sod. Carbonate | 0.06 | | |
| FD&C Yellow #6 | 0.10 | | |
| Magnesium Stearate | 0.75 | | |

EXAMPLE 3

This example illustrate a bilayer oral transmucosal tablet for long acting delivery of drugs formulated according to the method described in Example 1. The active substance in this example is Buprenorphine HCL, the penetration enhancer is taurocholic acid. The adhesive layer contains 60% non-plasticized PVP and 10% of an acrylic copolymer.

Buprenorphine HCL Long Acting

| Active Layer | % w/w | Adhesive Layer | % w/w |
|---|---|---|---|
| Buprenorphine HCL | 1.86 | Mannitol | 29.25 |
| Mannitol | 37.16 | Povidone K90 | 40.00 |
| Taurocholic Acid | 12.00 | Carbomer 934P | 10.00 |
| Klucel HXF | 30.00 | Povidone K30 | 20.00 |
| Carbomer 934P | 4.50 | Magnesium Stearate | 0.75 |
| Povidone K30 | 5.00 | | |
| Na Bicarbonate | 8.57 | | |
| Na Carbonate | 0.06 | | |
| FD&C Yellow #6 | 0.10 | | |
| Mg Stearate | 0.75 | | |

EXAMPLE 4

This example illustrate a bilayer oral transmucosal tablet for rapid onset delivery of drugs formulated according to the method described in Example 1. The active substance in this example is Fentanyl Citrate, the penetration enhancer is taurocholic acid. The adhesive layer contains 70% non-plasticized PVP.

Fentanyl Citrate

| Active Layer | % w/w | Adhesive Layer | % w/w |
|---|---|---|---|
| Fentanyl Citrate | 0.63 | Mannitol | 29.25 |
| Mannitol | 74.89 | Povidone K90 | 40.00 |
| Taurocholic Acid | 10.00 | Povidone K30 | 30.00 |
| Klucel HXF | 5.00 | Magnesium Stearate | 0.75 |
| Sodium Bicarbonate | 1.06 | | |
| Sodium Carbonate | 7.57 | | |
| FD&C Yellow #6 | 0.10 | | |
| Magnesium Stearate | 0.75 | | |

EXAMPLE 5

This example illustrate a bilayer oral transmucosal tablet for long acting delivery of drugs formulated according to the method described in Example 1. The active substance in this example is Fentanyl Citrate, the penetration enhancer is taurocholic acid. The adhesive layer contains about 70% non-plasticized PVP and 20% copolymer.

Fentanyl Citrate Long Acting

| Active Layer | % w/w | Adhesive Layer | % w/w |
|---|---|---|---|
| Fentanyl Citrate | 0.63 | Povidone K90 | 40.00 |
| Mannitol | 70.89 | Carbomer 934P | 20.00 |
| Taurocholic Acid | 10.00 | Povidone K30 | 39.25 |
| Carbomer 934P | 4.00 | Magnesium Stearate | 0.75 |
| Klucel HXF | 5.00 | | |
| Sod. Bicarbonate | 7.57 | | |
| Sod. Carbonate | 1.06 | | |
| FD&C Yellow #6 | 0.10 | | |
| Magnesium Stearate | 0.75 | | |

EXAMPLE 6

This example illustrate a bilayer oral transmucosal tablet for delivery of drugs formulated according to the method described in Example 1. The active substance in this example is DDAVP, the penetration enhancer is taurocholic acid. The adhesive layer contains about 70% non-plasticized PVP and 5% of an acrylic copolymer.

| OTM Tablet for DDAVP | | | |
|---|---|---|---|
| Active Layer | % w/w | Adhesive Layer | % w/w |
| DDAVP | 2.23 | Mannitol | 24.25 |
| Mannitol | 42.92 | Povidone K90 | 40.00 |
| Taurocholic Acid | 15.00 | Carbomer 934P | 5.00 |
| Magnasweet 100 | 15.00 | Povidone K30 | 30.00 |
| Klucel HXF | 24.00 | Magnesium Stearate | 0.75 |
| FD&C Yellow #6 | 0.10 | | |
| Magnesium Stearate | 0.75 | | |

EXAMPLE 7

This example illustrate a bilayer oral transmucosal tablet for delivery of drugs formulated according to the method described in Example 1. The active substance in this example is calcitonin, the penetration enhancer is taurocholic acid. The adhesive layer contains about 30% non-plasticized PVP and 20% of an acrylic copolymer.

| OTM Tablet for Calcitonin | | | |
|---|---|---|---|
| Active Layer | % w/w | Adhesive Layer | % w/w |
| Calcitonin | 3.01 | Mannitol | 49.25 |
| Mannitol | 60.29 | Povidone K90 | 20.00 |
| Taurocholic Acid | 5.00 | Carbomer 934P | 20.00 |
| Acelsulfame K | 1.00 | Povidone K30 | 10.00 |
| Klucel HXF | 30.00 | Magnesium Stearate | 0.75 |
| FD&C Yellow #6 | 0.20 | | |
| Magnesium Stearate | 0.50 | | |

EXAMPLE 8

This example illustrate a bilayer oral transmucosal tablet for breath refreshening formulated according to the method described in Example 1. The active substance in this example is menthol mint (50% by weight in active the layer and 30% by weight in the adhesive layer). The adhesive layer contains about 35% non-plasticized PVP.

| OTM Tablet of Menthol Mint for Breath Refreshening | | | |
|---|---|---|---|
| Active Layer | % w/w | Adhesive Layer | % w/w |
| Menthol Mint | 50.00 | Menthol Mint | 30.00 |
| Mannitol | 38.30 | Mannitol | 34.25 |
| Acelsulfame K | 1.00 | Povidone K90 | 25.00 |
| Povidone K30 | 10.00 | Povidone K30 | 10.00 |
| FD&C Yellow #6 | 0.20 | Magnesium Stearate | 0.75 |
| Magnesium Stearate | 0.50 | | |

EXAMPLE 9

This example illustrate a bilayer oral transmucosal tablet for breath refreshening formulated according to the method described in Example 1. The active substance in this example is licorice (20% by weight in the active layer and 30% by weight in the adhesive layer). The adhesive layer contains about 50% non-plasticized PVP.

| OTM Tablet of Licorice for Breath Refreshening | | | |
|---|---|---|---|
| Active Layer | % w/w | Adhesive Layer | % w/w |
| Licorice | 20.00 | Licorice | 30.00 |
| Mannitol | 44.30 | Mannitol | 19.25 |
| Magnasweet 100 | 5.00 | Povidone K90 | 30.00 |
| Xylitol | 30.00 | Povidone K30 | 20.00 |
| FD&C Yellow #6 | 0.20 | Magnesium Stearate | 0.75 |

EXAMPLE 10

This example illustrate a bilayer oral transmucosal tablet for long acting breath refreshening formulated according to the method described in Example 1. The active substance in this example is menthol mint (40% by weight in the active layer and 30% by weight in the adhesive layer). The adhesive layer contains about 40% non-plasticized PVP and 15% copolymer.

| OTM Tablet of Menthol Mint Long Acting | | | |
|---|---|---|---|
| Active Layer | % w/w | Adhesive Layer | % w/w |
| Menthol Mint | 40.00 | Menthol Mint | 30.00 |
| Mannitol | 49.30 | Mannitol | 14.25 |
| Acelsulfame K | 1.00 | Povidone K90 | 30.00 |
| Carbomer 934P | 4.00 | Povidone K30 | 10.00 |
| Methocel | 5.00 | Carbomer 934P | 15.00 |
| FD&C Yellow #6 | 0.20 | Magnesium Stearate | 0.75 |
| Magnesium Stearate | 0.50 | | |

EXAMPLE 11

This example illustrate a bilayer oral transmucosal tablet for breath refreshening and dry mouth relief formulated according to the method described in Example 1. The active substances in this example are eucalyptus oil in the active layer and spearmint in the adhesive layer. The adhesive layer contains a polymer combination of about 20% non-plasticized PVP and 15% copolymer.

| OTM Tablet of Eucalyptus and Spearmint | | | |
|---|---|---|---|
| Active Layer | % w/w | Adhesive Layer | % w/w |
| Eucalyptus Oil | 0.75 | Spearmint | 30.00 |
| Mannitol | 47.55 | Mannitol | 34.25 |
| Acelsulfame K | 1.00 | Povidone K90 | 10.00 |
| Klucel HXF | 50.00 | Carbomer 934P | 15.00 |
| FD&C Yellow #6 | 0.20 | Povidone K30 | 10.00 |
| Magnesium Stearate | 0.50 | Magnesium Stearate | 0.75 |

EXAMPLE 12

This example illustrate a bilayer oral transmucosal tablet for breath refreshening and dry mouth relief formulated according to the method described in Example 1. The active substances in this example is peppermint (40% by weight in the active layer and 30% by weight in the adhesive layer). The adhesive layer contains about 35% non-plasticized PVP.

| OTM Tablet of Peppermint for Breath Refreshening ||||
| --- | --- | --- | --- |
| Active Layer | % w/w | Adhesive Layer | % w/w |
| Peppermint | 40.00 | Peppermint | 30.00 |
| Lactose | 53.30 | Mannitol | 9.25 |
| Acelsulfame K | 1.00 | Povidone K90 | 50.00 |
| Methocel | 5.00 | Povidone K30 | 10.00 |
| FD&C Yellow #6 | 0.20 | Magnesium Stearate | 0.75 |
| Stearic Acid | 0.50 | | |

EXAMPLE 13

This example illustrate a bilayer oral transmucosal tablet for breath refreshening and dry mouth relief formulated according to the method described in Example 1. The active substances in this example is spearmint (30% by weight in the active layer and 30% by weight in the adhesive layer). The adhesive layer contains about 20% non-plasticized PVP and 15% copolymer.

| OTM Tablet of Spearmint for Breath Refreshening ||||
| --- | --- | --- | --- |
| Active Layer | % w/w | Adhesive Layer | % w/w |
| Spearmint | 30.00 | Spearmint | 30.00 |
| Mannitol | 38.30 | Mannitol | 34.25 |
| Acelsulfame K | 1.00 | Povidone K90 | 10.00 |
| Klucel HXF | 30.00 | Carbomer 934P | 15.00 |
| FD&C Yellow #6 | 0.20 | Povidone K30 | 10.00 |
| Stearic Acid | 0.50 | Stearic Acid | 0.75 |

While the above examples illustrate numerous embodiments of the invention, the scope of which is limited only by the operability exhibited by improved mucosal adhesive properties attributable to the non-plasticized PVP. The invention is not limited to any specific active substance or groups of substances as these are known in the art. Rather, the invention is drawn to the use of a non-plasticized PVP as a mucoadhesive for a transmucosal delivery device which has improved mucosal adhesive properties, e.g. It does not have an objectionable taste or interact with an ionic active substances to be delivered. It is, therefore, limited in scope only by the appended claims and their functional equivalents.

What is claimed is:

1. A device for the oral transmucosal delivery of active substances to the oral cavity comprising a mucoadhesive layer and at least one overlying active substance layer said mucoadhesive layer having one surface adapted to contact the mucosal surface of the oral cavity for adhering thereto and an opposing surface in contact with and adhering to an overlying active substance containing layer characterized in that the mucoadhesive layer contains a mucoadhesive composition comprising at least 50% by weight of a non-plasticized polyvinyl pyrrolidone polymer having a weight average molecular weight of between about 10,000 and 700,000.

2. A device according to claim 1 wherein said mucoadhesive layer contains from 20 to 99% by weight of said mucoadhesive composition.

3. A device according to claim 2 wherein said mucoadhesive composition consists of non-plasticized polyvinyl pyrrolidone polymer.

4. A device according to claim 2 wherein said mucoadhesive composition comprises about 50 to 95% by weight of non-plasticized polyvinyl pyrrolidone polymer and 5 to 50% by weight of an additional functionally suitable hydrophilic polymer or copolymer.

5. A device according to claim 4 wherein said additional hydrophilic polymer or copolymer is a member selected from the group consisting of acrylic acid polymers, hydroxypropyl cellulose, methylcellulose, polyethylene oxide, polyvinyl pyrrolidone, gaur-gum, pectins, starches, gelatin and casein.

6. A device according to claim 3 or 4 wherein the overlying active substance layer contains from about 3 to 60% by weight of a hydrophilic polymer in which the active substance is intimately contained.

7. A device according to claim 6 wherein the active substance is a breath freshener and is present in the active substance layer in amounts of between about 10 to 60% by weight.

8. A device according to claim 7 wherein the mucoadhesive layer also contains an active substance in amounts of between about 5 to 40% by weight.

9. A device according to claim 8 wherein the mucoadhesive composition content of the mucoadhesive layer is present in amounts of between about 20 to 60% by weight.

10. A device according to claim 9 wherein the breath freshener is an odorant member selected from the group consisting of peppermint, spearmint, menthol, grape, cherry, lemon, strawberry, orange, licorice, lime and any mixtures thereof.

11. A device according to claim 8 wherein the surface area of said mucoadhesive layer adapted for contact with the mucosal surface is between about 0.5 and 10 cm$^2$.

12. A device according to claim 11 wherein said device is a tablet.

13. A device according to claim 12 wherein the thickness of the mucoadhesive layer is between about 0.1 and 3 mm.

14. A device according to claim 6 wherein the active substance is a drug and is present in the active substance layer in amounts of between about 0.1 to 10% by weight.

15. A device according to claim 14 wherein the drug is an ionic drug.

16. A device according to claim 15 wherein said ionic drug is a peptide.

17. A device according to claim 14 wherein the mucoadhesive layer also contains a chemical permeation enhancer in amounts of between about 2 to 20% by weight.

18. A device according to claim 17 wherein the chemical permeation enhancer is a bile acid or a salt thereof.

19. A device according to claim 18 wherein said drug is an ionic drug.

20. A device according to claim 19 wherein said ionic drug is a peptide.

21. A device according to claim 14 wherein the surface area of said mucoadhesive layer adapted for contact with the mucosal surface is between about 0.5 and 10 cm$^2$.

22. A device according to claim 21 wherein said device is a tablet.

23. A device according to claim 22 wherein the thickness of the mucoadhesive layer is between about 0.1 and 3 mm.

24. A method for the oral transmucosal delivery of active substances to the oral cavity comprising the steps of:
   a) applying to the mucosa of said oral cavity a device comprising a mucoadhesive layer and at least one overlying active substance layer said mucoadhesive layer having one surface which is in contact with the mucosal surface of the oral cavity and adhering thereto and having an opposing surface in contact with and adhering to an overlying active substance containing layer characterized in that the mucoadhesive layer contains a mucoadhesive composition comprising at least 50% by weight of a non-plasticized polyvinyl pyrrolidone polymer having a weight average molecular weight of between about 10,000 and 700,000; and b) retaining said device adhering to said mucosa until said active substance has been released in said oral cavity.

25. A method according to claim 24 wherein said mucoadhesive layer contains from 20 to 99% by weight of said mucoadhesive composition.

26. A method according to claim 25 wherein said mucoadhesive composition consists of non-plasticized polyvinyl pyrrolidone polymer.

27. A method according to claim 25 wherein said mucoadhesive composition comprises about 50 to 95% by weight of non-plasticized polyvinyl pyrrolidone polymer and 5 to 50% by weight of an additional functionally suitable hydrophilic polymer or copolymer.

28. A method according to claim 27 wherein said additional hydrophilic polymer or copolymer is a member selected from the group consisting of acrylic acid polymers, hydroxypropyl cellulose, methylcellulose, polyethylene oxide, polyvinyl pyrrolidone, gaur-gum, pectins, starches, gelatin and casein.

29. A method according to claim 26 or 27 wherein the overlying active substance layer contains from about 3 to 60% by weight of a hydrophilic polymer in which the active substance is intimately contained.

30. A method according to claim 29 wherein the active substance is a breath freshener and is present in the active substance layer in amounts of between about 10 to 60% by weight.

31. A method according to claim 30 wherein the mucoadhesive layer also contains an active substance in amounts of between about 5 to 40% by weight.

32. A method according to claim 31 wherein the mucoadhesive composition content of the mucoadhesive layer is present in amounts of between about 20 to 60% by weight.

33. A method according to claim 32 wherein the device is adhered to the hard palate.

34. A method according to claim 33 wherein the breath freshener is an odorant member selected from the group consisting of peppermint, spearmint, menthol, grape, cherry, lemon, strawberry, orange, licorice, lime and any mixtures thereof.

35. A method according to claim 33 wherein the surface area of said mucoadhesive layer adapted for contact with the mucosal surface is between about 0.5 and 10 $cm^2$.

36. A method according to claim 35 wherein said device is a tablet.

37. A method according to claim 36 wherein the thickness of the mucoadhesive layer is between about 0.1 and 3 mm.

38. A method according to claim 30 wherein the active substance is a drug and is present in the active substance layer in amounts of between about 0.1 to 10% by weight.

39. A method according to claim 38 wherein the drug is an ionic drug.

40. A method according to claim 39 wherein said ionic drug is a peptide.

41. A method according to claim 38 wherein the mucoadhesive layer also contains a chemical permeation enhancer in amounts of between about 2 to 20% by weight.

42. A method according to claim 41 wherein the chemical permeation enhancer is a bile acid or a salt thereof.

43. A method according to claim 42 wherein said drug is an ionic drug.

44. A method according to claim 43 wherein said ionic drug is a peptide.

45. A method according to claim 38 wherein the surface area of said mucoadhesive layer adapted for contact with the mucosal surface is between about 0.5 and 10 $cm^2$.

46. A method according to claim 45 wherein said device is a tablet.

47. A method according to claim 46 wherein the thickness of the mucoadhesive layer is between about 0.1 and 3 mm.

* * * * *